United States Patent
Jeong et al.

(10) Patent No.: US 9,517,936 B2
(45) Date of Patent: Dec. 13, 2016

(54) QUANTUM DOT STABILIZED BY HALOGEN SALT AND METHOD FOR MANUFACTURING THE SAME

(71) Applicant: KOREA INSTITUTE OF MACHINERY & MATERIALS, Daejeon (KR)

(72) Inventors: Sohee Jeong, Daejeon (KR); Ju Young Woo, Gyeonggi-do (KR); Doh Chang Lee, Daejeon (KR); Won Seok Chang, Daejeon (KR); Duck Jong Kim, Daejeon (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 0 days.

(21) Appl. No.: 14/677,999

(22) Filed: Apr. 3, 2015

(65) Prior Publication Data
US 2015/0291422 A1 Oct. 15, 2015

(30) Foreign Application Priority Data
Apr. 11, 2014 (KR) .................. 10-2014-0043638

(51) Int. Cl.
| | | |
|---|---|---|
| *C07F 7/00* | (2006.01) | |
| *C01B 19/00* | (2006.01) | |
| *C07C 57/12* | (2006.01) | |
| *C07C 51/41* | (2006.01) | |
| *C01B 21/06* | (2006.01) | |
| *C01B 21/072* | (2006.01) | |
| *B82Y 40/00* | (2011.01) | |
| *B82Y 30/00* | (2011.01) | |

(52) U.S. Cl.
CPC .......... *C01B 19/002* (2013.01); *C01B 19/007* (2013.01); *C01B 21/06* (2013.01); *C01B 21/0632* (2013.01); *C01B 21/072* (2013.01); *C07C 51/418* (2013.01); *C07C 57/12* (2013.01); *B82Y 30/00* (2013.01); *B82Y 40/00* (2013.01); *C01P 2004/64* (2013.01); *Y10S 977/774* (2013.01); *Y10S 977/896* (2013.01)

(58) Field of Classification Search
CPC ............................ C01B 19/002; C07C 51/418
USPC ........................................................ 556/105
See application file for complete search history.

(56) References Cited

PUBLICATIONS

Traub et al., J. Am. Chem. Soc. 2008, 130, 955-964.*
Peng et al., J. Am. Chem. Soc. 1997, 119, 7019-7029.*
Bae et al., J. Am. Chem. Soc. 2012, 134, 20160-20168.*
Wan Ki Bae et al., "Highly Effective Surface Passivation of PbSe Quantum Dots through Reaction with Molecular Chlorine," J. Am. Chem.Soc., 2012, 134, pp. 20160-20168.
Aaron T. Fafarman et al., "Air-Stable, Nanostructured Electronic and Plasmonic Materials from Solution-Processable, Silver Nanocrystal Building Blocks," American Chemical Society, 2014, vol. 8, No. 3, pp. 2746-2754, www.acsnano.org.

* cited by examiner

*Primary Examiner* — Porfirio Nazario Gonzalez
*Assistant Examiner* — Kofi Adzamli
(74) *Attorney, Agent, or Firm* — Hauptman Ham, LLP (57) ABSTRACT

A quantum dot stabilized by a halogen salt includes a compound of Group 13 and Group 15, a compound of Group 12 and Group 16 or a compound of Group 14 and Group 16. The quantum dot has a crystalline structure and at least a portion of a surface of the quantum dot is combined with a halogen salt. Thus, the quantum dot has a high stability in an air.

6 Claims, 7 Drawing Sheets

QUANTUM DOT STABILIZED BY HALOGEN SALT AND METHOD FOR MANUFACTURING THE SAME

CROSS-REFERENCE TO RELATED APPLICATIONS

This application claims priority under 35 U.S.C. §119 to Korean Patent Application No. 10-2014-0043638, filed on Apr. 11, 2014, and all the benefits accruing therefrom, the content of which is herein incorporated by reference in its entirety.

BACKGROUND

1. Field

Exemplary embodiments relate to a quantum dot. More particularly, exemplary embodiments relate to a quantum dot stabilized by a halogen salt and a method for manufacturing the quantum dot.

2. Description of the Related Art

A quantum dot is a nano-particle having semiconductive properties and having a size less than tens of nanometers. The quantum dot has properties different from a bulk particle due to quantum confinement effect. For example, the quantum dot can change a wavelength of a light, which the quantum dot absorbs, according to a size thereof. Furthermore, the quantum dot has novel optical, electrical and physical properties that the bulk particle does not have. Thus, researches are being conducted for manufacturing a photoelectric conversion device such as a solar cell, a light-emitting diode or the like.

Recently, a colloidal chemosynthesis has been developed for controlling a size and a shape of the quantum dot. However, the quantum dot manufactured by the colloidal chemosynthesis has a low stability in an air. A core-shell quantum dot having a thick skin may be relatively stable in an air. However, the core-shell quantum dot is hardly applicable for the photoelectric conversion device, and manufacturing processes for the core-shell quantum dot are complicated.

SUMMARY

Exemplary embodiments provide a quantum dot stable in an air.

Exemplary embodiments also provide a method for manufacturing the quantum dot.

According to an exemplary embodiment, a quantum dot stabilized by a halogen salt includes a compound of Group 13 and Group 15, a compound of Group 12 and Group 16 or a compound of Group 14 and Group 16. The quantum dot has a crystalline structure, and at least a portion of a surface of the quantum dot is combined with a halogen salt.

In an exemplary embodiment, a diameter of the quantum dot is 1 nm to 20 nm.

In an exemplary embodiment, the quantum dot has a first surface combined with the halogen salt and a second surface combined with an organic ligand.

In an exemplary embodiment, a (100) surface is combined with the halogen salt, and a (111) surface is combined with the organic ligand.

In an exemplary embodiment, the compound of Group 14 and Group 16 includes at least one selected from the group consisting of tin oxide (SnO), tin sulfide (SnS), tin selenide (SnSe), tin telluride (SnTe), lead sulfide (PbS), lead selenide (PbSe), lead telluride (PbTe), germanium oxide (GeO), germanium sulfide (GeS), germanium selenide (GeSe), germanium telluride (GeTe), tin selenium sulfide (SnSeS), tin selenium telluride (SnSeTe), tin sulfide telluride (SnSTe), lead selenium sulfide (PbSeS), lead selenium telluride (PbSeTe), lead sulfide telluride (PbSTe), tin lead sulfide (SnPbS), tin lead selenide (SnPbSe), tin lead telluride (SnPbTe), tin oxide sulfide (SnOS), tin oxide selenide (SnOSe), tin oxide telluride (SnOTe), germanium oxide sulfide (GeOS), germanium oxide selenide (GeOSe), germanium oxide telluride (GeOTe), tin lead sulfide selenide (SnPbSSe), tin lead selenium telluride (SnPbSeTe) and tin lead sulfide telluride (SnPbSTe).

In an exemplary embodiment, the compound of Group 13 and Group 15 includes at least one selected from the group consisting of gallium phosphide (GaP), gallium arsenide (GaAs), gallium antimonide (GaSb), gallium nitride (GaN), aluminum phosphide (AlP), aluminum arsenide (AlAs), aluminum antimonide (AlSb), aluminum nitride (AlN), indium phosphide (InP), indium arsenide (InAs), indium antimonide (InSb), indium nitride (InN), gallium phosphide arsenide (GaPAs), gallium phosphide antimonide (GaPSb), gallium phosphide nitride (GaPN), gallium arsenide nitride (GaAsN), gallium antimonide nitride (GaSbN), aluminum phosphide arsenide (AlPAs), aluminum phosphide antimonide (AlPSb), aluminum phosphide nitride (AlPN), aluminum arsenide nitride (AlAsN), aluminum antimonide nitride (AlSbN), indium phosphide arsenide (InPAs), indium phosphide antimonide (InPSb), indium phosphide nitride (InPN), indium arsenide nitride (InAsN), indium antimonide nitride (InSbN), aluminum gallium phosphide (AlGaP), aluminum gallium arsenide (AlGaAs), aluminum gallium antimonide (AlGaSb), aluminum gallium nitride (AlGaN), aluminum arsenide nitride (AlAsN), aluminum antimonide nitride (AlSbN), indium gallium phosphide (InGaP), indium gallium arsenide (InGaAs), indium gallium antimonide (InGaSb), indium gallium nitride (InGaN), indium arsenide nitride (InAsN), indium antimonide nitride (InSbN), aluminum indium phosphide (AlInP), aluminum indium arsenide (AlInAs), aluminum indium antimonide (AlInSb), aluminum indium nitride (AlInN), aluminum arsenide nitride (AlAsN), aluminum antimonide nitride (AlSbN), aluminum phosphide nitride (AlPN), gallium aluminum phosphide arsenide (GaAlPAs), gallium aluminum phosphide antimonide (GaAlPSb), gallium indium phosphide arsenide (GaInPAs), gallium indium aluminum arsenide (GaInAlAs), gallium aluminum phosphide nitride (GaAlPN), gallium aluminum arsenide nitride (GaAlAsN), gallium aluminum antimonide nitride (GaAlSbN), gallium indium phosphide nitride (GaInPN), gallium indium arsenide nitride (GaInAsN), gallium indium aluminum nitride (GaInAlN), gallium antimonide phosphide nitride (GaSbPN), gallium arsenide phosphide nitride (GaAsPN), gallium arsenide antimonide nitride (GaAsSbN), gallium indium phosphide antimonide (GaInPSb), gallium indium phosphide nitride (GaInPN), gallium indium antimonide nitride (GaInSbN), gallium phosphide antimonide nitride (GaPSbN), indium aluminum phosphide arsenide (InAlPAs), indium aluminum phosphide nitride (InAlPN), indium phosphide arsenide nitride (InPAsN), indium aluminum antimonide nitride (InAlSbN), indium phosphide antimonide nitride (InPSbN), indium arsenide antimonide nitride (InAsSbN) and indium aluminum phosphide antimonide (InAlPSb).

In an exemplary embodiment, the compound of Group 12 and Group 16 includes at least one selected from the group consisting of cadmium sulfide (CdS), cadmium selenide (CdSe), cadmium telluride (CdTe), zinc sulfide (ZnS), zinc selenide (ZnSe), zinc telluride (ZnTe), mercury sulfide (HgS), mercury selenide (HgSe), mercury telluride (HgTe), zinc oxide (ZnO), cadmium oxide (CdO), mercury oxide (HgO), cadmium selenium sulfide (CdSeS), cadmium selenium telluride (CdSeTe), cadmium sulfide telluride (CdSTe), cadmium zinc sulfide (CdZnS), cadmium zinc selenide (CdZnSe), cadmium sulfide selenide (CdSSe), cadmium zinc telluride (CdZnTe), cadmium mercury sulfide (CdHgS), cadmium mercury selenide (CdHgSe), cadmium mercury telluride (CdHgTe), zinc selenium sulfide (ZnSeS), zinc selenium telluride (ZnSeTe), zinc sulfide telluride (ZnSTe), mercury selenium sulfide (HgSeS), mercury selenium telluride (HgSeTe), mercury sulfide telluride (HgSTe), mercury zinc sulfide (HgZnS), mercury zinc selenide (HgZnSe), cadmium zinc oxide (CdZnO), cadmium mercury oxide (CdHgO), zinc mercury oxide (ZnHgO), zinc selenium oxide (ZnSeO), zinc tellurium oxide (ZnTeO), zinc sulfide oxide (ZnSO), cadmium selenium oxide (CdSeO), cadmium tellurium oxide (CdTeO), cadmium sulfide oxide (CdSO), mercury selenium oxide (HgSeO), mercury tellurium oxide (HgTeO), mercury sulfide oxide (HgSO), cadmium zinc selenium sulfide (CdZnSeS), cadmium zinc selenium telluride (CdZnSeTe), cadmium zinc sulfide telluride (CdZnSTe), cadmium mercury selenium sulfide (CdHgSeS), cadmium mercury selenium telluride (CdHgSeTe), cadmium mercury sulfide telluride (CdHgSTe), mercury zinc selenium sulfide (HgZnSeS), mercury zinc selenium telluride (HgZnSeTe), mercury zinc sulfide telluride (HgZnSTe), cadmium zinc selenium oxide (CdZnSeO), cadmium zinc tellurium oxide (CdZnTeO), cadmium zinc sulfide oxide (CdZnSO), cadmium mercury selenium oxide (CdHgSeO), cadmium mercury tellurium oxide (CdHgTeO), cadmium mercury sulfide oxide (CdHgSO), zinc mercury selenium oxide (ZnHgSeO), zinc mercury tellurium oxide (ZnHgTeO) and zinc mercury sulfide oxide (ZnHgSO).

According to an exemplary embodiment, a method for manufacturing a quantum dot includes forming a quantum dot particle including a compound of Group 13 and Group 15, a compound of Group 12 and Group 16 or a compound of Group 14 and Group 16, and providing a halogen compound to the quantum dot particle to stabilize the quantum dot particle.

In an exemplary embodiment, forming the quantum dot particle includes reacting a first precursor with an organic acid, and reacting a second precursor with a reaction product of the first precursor and the organic acid.

In an exemplary embodiment, the first precursor includes an element of Group 12, Group 13 or group 14.

In an exemplary embodiment, the organic acid includes at least one selected from the group consisting of formic acid, acetic acid, propionic acid, valeric acid, butyric acid, hexanoic acid, caprylic acid, capric acid and lauric acid.

In an exemplary embodiment, the second precursor includes an element of Group 15 or group 16.

In an exemplary embodiment, the halogen compound includes at least one selected from the group consisting of a chloride, a bromide and an iodide.

In an exemplary embodiment, the halogen compound includes at least one selected from the group consisting of tetrabutylammonium bromide, cetyltrimethylammonium bromide, ammonium chloride, ammonium bromide, ammonium iodide, potassium chloride, potassium bromide, potassium iodide, sodium chloride, sodium bromide, sodium iodide, indium chloride, indium bromide and indium iodide.

According to the exemplary embodiments, a quantum dot having increased stability in an air may be obtained.

BRIEF DESCRIPTION OF THE DRAWINGS

The above and other features and advantages will become more apparent by describing exemplary embodiments thereof with reference to the accompanying drawings, in which.

DETAILED DESCRIPTION

Example embodiments are described more fully hereinafter with reference to the accompanying drawings. The inventive concept may, however, be embodied in many different forms and should not be construed as limited to the example embodiments set forth herein. In the drawings, the sizes and relative sizes of layers and regions may be exaggerated for clarity. It will be understood that, although the terms first, second, third etc. may be used herein to describe various elements, components, regions, layers, patterns and/or sections, these elements, components, regions, layers, patterns and/or sections should not be limited by these terms. These terms are only used to distinguish one element, component, region, layer pattern or section from another region, layer, pattern or section. Thus, a first element, component, region, layer or section discussed below could be termed a second element, component, region, layer or section without departing from the teachings of example embodiments.

Example embodiments are described herein with reference to cross sectional illustrations that are schematic illustrations of illustratively idealized example embodiments (and intermediate structures) of the inventive concept. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. The regions illustrated in the figures are schematic in nature and their shapes are not intended to illustrate the actual shape of a region of a device and are not intended to limit the scope of the inventive concept.

The terminology used herein is for the purpose of describing particular example embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Quantum Dot Stabilized by a Halogen Salt

A quantum dot according to an exemplary embodiment of the present invention has a crystalline structure and includes at least two elements. At least a portion of a surface of the quantum dot is covered by a halogen salt. The quantum dot may include a bond of a metal and a semi-metal or a bond of a metal and a non-metal. The halogen salt may include an ionic bond of a metal atom that belongs to the quantum dot and a halogen atom.

Figure 1:
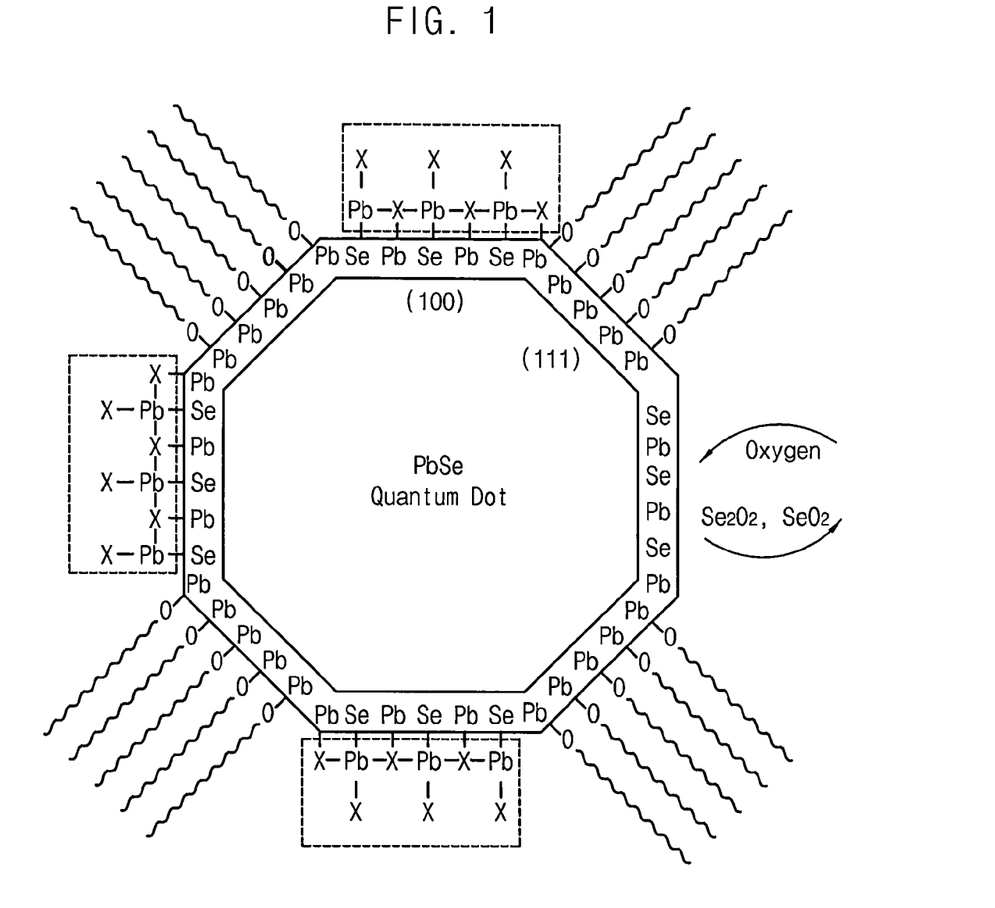
FIG. 1 is a schematic view illustrating a structure of a quantum dot according to an exemplary embodiment of the present invention.

FIG. 1 is a schematic view illustrating a structure of a quantum dot according to an exemplary embodiment of the present invention. Referring to FIG. 1, a quantum dot may include lead selenide (PbSe). For example, PbSe quantum dot may have a rock-salt cubic crystalline structure. The quantum dot has a (100) surface and a (111) surface. Lead atoms are arranged at the (111) surface, and are combined with a ligand to be stabilized. Since lead atoms and selenium atoms are arranged at the (100) surface, the (100) surface has relatively low stability in an air. Thus, if the (100) surface is not protected, the selenium atoms of the (100) surface may be oxidized or separated thereby causing deterioration or damage of a quantum dot. However, the quantum dot according to an exemplary embodiment of the present invention includes a halogen salt combined with the (100) surface. Thus, the quantum dot may have increased stability in an air.

The halogen salt may be halogenated lead (PbX) including a halogen atom combined with a lead atom. The halogen salt may form a mono-layered structure or a multiple-layered structure on the (100) surface. The quantum dot may have a diameter of about 1 nm to about 100 nm, preferably about 1 nm to about 20 nm.

Examples of the halogen may include fluorine, chlorine, bromine, iodine or the like. For example, the halogen salt may include lead chloride, lead bromide, lead iodide, lead fluoride or combination thereof. Since lead fluoride ($PbF_2$) has a relatively large bond energy, applicability of a quantum dot including lead fluoride may be reduced. Thus, lead chloride, lead bromide, lead iodide may be preferred to lead fluoride.

Combination of the ligand and a lead atom may form a bond of Pb—O on the (111) surface. The ligand may be an organic ligand or an inorganic ligand. Preferably, the ligand may be an organic ligand provided by an organic acid such as oleic acid. The organic ligand may include carbon atoms equal to or less than 20.

In the embodiment, the quantum dot includes PbSE, and the (111) surface is combined with the organic ligand, and the (100) surface is combined with the halogen salt. However, exemplary embodiments of the present invention are not limited thereto, and may change according to elements and crystalline structures. Exemplary embodiments of the present invention may include various quantum dot including a first surface combined with an organic ligand, and a second surface, which is not combined with the organic ligand, combined with a halogen salt.

The quantum dot may include various combinations of materials besides PbSe. For example, the quantum dot may include a compound of Group 14 and Group 16 (in the periodic table). For example, the quantum dot may include tin oxide (SnO), tin sulfide (SnS), tin selenide (SnSe), tin telluride (SnTe), lead sulfide (PbS), lead selenide (PbSe), lead telluride (PbTe), germanium oxide (GeO), germanium sulfide (GeS), germanium selenide (GeSe), germanium telluride (GeTe), tin selenium sulfide (SnSeS), tin selenium telluride (SnSeTe), tin sulfide telluride (SnSTe), lead selenium sulfide (PbSeS), lead selenium telluride (PbSeTe), lead sulfide telluride (PbSTe), tin lead sulfide (SnPbS), tin lead selenide (SnPbSe), tin lead telluride (SnPbTe), tin oxide sulfide (SnOS), tin oxide selenide (SnOSe), tin oxide telluride (SnOTe), germanium oxide sulfide (GeOS), germanium oxide selenide (GeOSe), germanium oxide telluride (GeOTe), tin lead sulfide selenide (SnPbSSe), tin lead selenium telluride (SnPbSeTe), tin lead sulfide telluride (SnPbSTe) or the like. Theses may be used each alone or in a combination thereof.

In another embodiment, the quantum dot may include a compound of Group 12 and Group 16. For example, the quantum dot may include cadmium sulfide (CdS), cadmium selenide (CdSe), cadmium telluride (CdTe), zinc sulfide (ZnS), zinc selenide (ZnSe), zinc telluride (ZnTe), mercury sulfide (HgS), mercury selenide (HgSe), mercury telluride (HgTe), zinc oxide (ZnO), cadmium oxide (CdO), mercury oxide (HgO), cadmium selenium sulfide (CdSeS), cadmium selenium telluride (CdSeTe), cadmium sulfide telluride (CdSTe), cadmium zinc sulfide (CdZnS), cadmium zinc selenide (CdZnSe), cadmium sulfide selenide (CdSSe), cadmium zinc telluride (CdZnTe), cadmium mercury sulfide (CdHgS), cadmium mercury selenide (CdHgSe), cadmium mercury telluride (CdHgTe), zinc selenium sulfide (ZnSeS), zinc selenium telluride (ZnSeTe), zinc sulfide telluride (ZnSTe), mercury selenium sulfide (HgSeS), mercury selenium telluride (HgSeTe), mercury sulfide telluride (HgSTe), mercury zinc sulfide (HgZnS), mercury zinc selenide (HgZnSe), cadmium zinc oxide (CdZnO), cadmium mercury oxide (CdHgO), zinc mercury oxide (ZnHgO), zinc selenium oxide (ZnSeO), zinc tellurium oxide (ZnTeO), zinc sulfide oxide (ZnSO), cadmium selenium oxide (CdSeO), cadmium tellurium oxide (CdTeO), cadmium sulfide oxide (CdSO), mercury selenium oxide (HgSeO), mercury tellurium oxide (HgTeO), mercury sulfide oxide (HgSO), cadmium zinc selenium sulfide (CdZnSeS), cadmium zinc selenium telluride (CdZnSeTe), cadmium zinc sulfide telluride (CdZnSTe), cadmium mercury selenium sulfide (CdHgSeS), cadmium mercury selenium telluride (CdHgSeTe), cadmium mercury sulfide telluride (CdHgSTe), mercury zinc selenium sulfide (HgZnSeS), mercury zinc selenium telluride (HgZnSeTe), mercury zinc sulfide telluride (HgZnSTe), cadmium zinc selenium oxide (CdZnSeO), cadmium zinc tellurium oxide (CdZnTeO), cadmium zinc sulfide oxide (CdZnSO), cadmium mercury selenium oxide (CdHgSeO), cadmium mercury tellurium oxide (CdHgTeO), cadmium mercury sulfide oxide (CdHgSO), zinc mercury selenium oxide (ZnHgSeO), zinc mercury tellurium oxide (ZnHgTeO), zinc mercury sulfide oxide (ZnHgSO) or the like. Theses may be used each alone or in a combination thereof.

In another embodiment, the quantum dot may include a compound of Group 13 and Group 15. For example, the quantum dot may include gallium phosphide (GaP), gallium arsenide (GaAs), gallium antimonide (GaSb), gallium nitride (GaN), aluminum phosphide (AlP), aluminum arsenide (AlAs), aluminum antimonide (AlSb), aluminum nitride (AlN), indium phosphide (InP), indium arsenide (InAs), indium antimonide (InSb), indium nitride (InN), gallium phosphide arsenide (GaPAs), gallium phosphide antimonide (GaPSb), gallium phosphide nitride (GaPN), gallium arsenide nitride (GaAsN), gallium antimonide nitride (GaSbN), aluminum phosphide arsenide (AlPAs), aluminum phosphide antimonide (AlPSb), aluminum phosphide nitride (AlPN), aluminum arsenide nitride (AlAsN), aluminum antimonide nitride (AlSbN), indium phosphide arsenide (InPAs), indium phosphide antimonide (InPSb), indium phosphide nitride (InPN), indium arsenide nitride (InAsN), indium antimonide nitride (InSbN), aluminum gallium phosphide (AlGaP), aluminum gallium arsenide (AlGaAs), aluminum gallium antimonide (AlGaSb), aluminum gallium nitride (AlGaN), aluminum arsenide nitride (AlAsN), aluminum antimonide nitride (AlSbN), indium gallium phosphide (InGaP), indium gallium arsenide (InGaAs), indium gallium antimonide (InGaSb), indium gallium nitride (InGaN), indium arsenide nitride (InAsN), indium antimonide nitride (InSbN), aluminum indium phosphide (AlInP), aluminum indium arsenide (AlInAs), aluminum indium antimonide (AlInSb), aluminum indium nitride (AlInN), aluminum arsenide nitride (AlAsN), aluminum antimonide nitride (AlSbN), aluminum phosphide nitride (AlPN), gallium aluminum phosphide arsenide (GaAlPAs), gallium aluminum phosphide antimonide (GaAlPSb), gallium indium phosphide arsenide (GaInPAs), gallium indium aluminum arsenide (GaInAlAs), gallium aluminum phosphide nitride (GaAlPN), gallium aluminum arsenide nitride (GaAlAsN), gallium aluminum antimonide nitride (GaAlSbN), gallium indium phosphide nitride (GaInPN), gallium indium arsenide nitride (GaInAsN), gallium indium aluminum nitride (GaInAlN), gallium antimonide phosphide nitride (GaSbPN), gallium arsenide phosphide nitride (GaAsPN), gallium arsenide antimonide nitride (GaAsSbN), gallium indium phosphide antimonide (GaInPSb), gallium indium phosphide nitride (GaInPN), gallium indium antimonide nitride (GaInSbN), gallium phosphide antimonide nitride (GaPSbN), indium aluminum phosphide arsenide (InAlPAs), indium aluminum phosphide nitride (InAlPN), indium phosphide arsenide nitride (InPAsN), indium aluminum antimonide nitride (InAlSbN), indium phosphide antimonide nitride (InPSbN), indium arsenide antimonide nitride (InAsSbN), indium aluminum phosphide antimonide (InAlPSb) or the like. Theses may be used each alone or in a combination thereof.

The quantum dot may be stable in an air even without a thick skin layer. Thus, applicability and electric properties may be improved.

Method for Manufacturing a Quantum Dot

Figure 2:
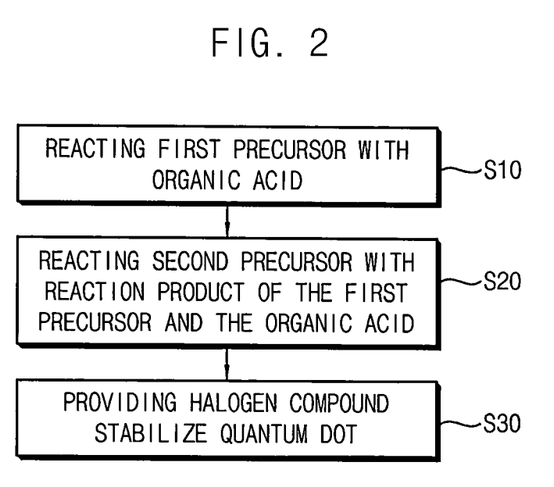
FIG. 2 is a flow chart illustrating a method for manufacturing a quantum dot according to an exemplary embodiment of the present invention.

FIG. 2 is a flow chart illustrating a method for manufacturing a quantum dot according to an exemplary embodiment of the present invention.

Referring to FIG. 2, a first precursor reacts with an organic acid (S10). For example, the first precursor and the organic acid are dispersed in a solvent. The first precursor may include at least one element selected from Groups 12, 13 and 14.

For example, the first precursor including an element of Group 12 may include cadmium acetate dihydrate, dimethyl cadmium, diethyl cadmium, cadmium acetate, cadmium acetylacetonate, cadmium acetylacetonate hydrate, cadmium iodide, cadmium bromide, cadmium chloride, cadmium chloride hydrate, cadmium fluoride, cadmium carbonate, cadmium nitrate, cadmium nitrate tetrahydrate, cadmium oxide, cadmium perchlorate, cadmium perchlorate hexahydrate, cadmium phosphide, cadmium sulfate, cadmium naphthenate, cadmium stearate, dimethyl zinc, diethyl zinc, zinc acetate, zinc acetate dihydrate, zinc acetylacetonate, zinc acetylacetonate hydrate, zinc iodide, zinc bromide, zinc chloride, zinc fluoride, zinc fluoride tetrahydrate, zinc carbonate, zinc cyanide, zinc nitrate, zinc nitrate hexahydrate, zinc oxide, zinc peroxide, zinc perchlorate, zinc perchlorate hexahydrate, zinc sulfate, diphenyl zinc, zinc naphthenate, zinc stearate, mercury acetate, mercury iodide, mercury bromide, mercury chloride, mercury fluoride, mercury cyanide, mercury nitrate, mercury nitrate monohydrate, mercury oxide, mercury perchlorate, mercury perchlorate tetrahydrate, mercury perchlorate trihydrate, mercury sulfate, dimethyl mercury, diethyl mercury, diphenyl mercury, mercury sulfate, mercury trifluoromethane sulfonate, methylmercury chloride, methylmercury iodide, phenylmercury acetate, phenylmercury chloride or the like. Theses may be used each alone or in a combination thereof.

For example, the first precursor including an element of Group 13 may include aluminum acetate, aluminum iodide, aluminum bromide, aluminum chloride, aluminum chloride hexahydrate, aluminum fluoride, aluminum nitrate, aluminum oxide, aluminum perchlorate, aluminum carbide, aluminum stearate, aluminum sulfate, di-i-butylaluminum chloride, diethylaluminum chloride, tri-i-butylaluminum, triethylaluminum, triethyl(tri-sec-butoxy)dialuminum, trimethylaluminum, gallium acetylacetonate, gallium chloride, gallium fluoride, gallium fluoride trihydrate, gallium oxide, gallium nitrate, gallium nitrate hydrate, gallium sulfate, gallium iodide, triethyl gallium, trimethyl gallium, indium chloride, indium chloride tetrahydrate, indium oxide, indium nitrate, indium nitrate hydrate, indium sulfate, indium sulfate hydrate, indium acetate, indium acetylacetonate, indium bromide, indium fluoride, indium fluoride trihydrate, trimethyl indium or the like. Theses may be used each alone or in a combination thereof.

For example, the first precursor including an element of Group 14 may include lead acetate, lead acetate trihydrate, lead bromide, lead chloride, lead fluoride, lead oxide, lead perchlorate, lead nitrate, lead sulfate, lead carbonate, lead acethylacetonate, lead citrate, lead bromide, lead naphthenate, tin acetate, tin bisacetylacetonate, tin bromide, tin chloride, tin chloride dihydrate, tin chloride pentahydrate, tin fluoride, tin oxide, tin sulfate, tin iodide, diphenyltin dichloride, germanium tetrachloride, germanium oxide, germanium ethoxide, germanium bromide, germanium iodide, tetramethyl germanium, trimethyl germanium chloride, trimethyl germanium bromide, triethyl germanium chloride or the like. Theses may be used each alone or in a combination thereof.

In an exemplary embodiment, the organic acid may include oleic acid.

In another exemplary embodiment, the organic acid may include a low molecular weight organic acid. For example, the low molecular weight organic acid may include formic acid, acetic acid, propionic acid, valeric acid, butyric acid, hexanoic acid, caprylic acid, capric acid, lauric acid or the like. Theses may be used each alone or in a combination thereof.

In another exemplary embodiment, the organic acid may include a mixture of the low molecular weight organic acid and oleic acid. A mole ratio of the low molecular weight organic acid and oleic acid may be about 10:1 to about 1:1, preferably about 9:1 to about 7:3. When the organic acid includes only the low molecular weight organic acid, or when the ratio of the low molecular weight organic acid to oleic acid is excessively large, a size of the quantum dot may increase to deteriorate photoelectric properties. When the ratio of the low molecular weight organic acid to oleic acid is excessively small, stability of the quantum dot in an air may be decreased.

Furthermore, when the organic acid includes a mixture of the low molecular weight organic acid and oleic acid, a size and a shape of the quantum dot may be easily controlled by adjusting the mole ratio of the low molecular weight organic acid and oleic acid.

In another exemplary embodiment, the organic acid may include a mixture of oleic acid and a halogen compound. The halogen compound may react with the first precursor to form a halogen ligand. For example, the halogen compound may include ammonium chloride, ammonium bromide or the like.

The solvent may be an organic solvent. For example, the solvent may include a hydrocarbon, an amine or the like.

For example, the hydrocarbon may include hexane, dodecane, decane, undecane, tetradecane, hexadecane, 1-hexadecyne, 1-octadecyne, diphenylether or the like. Theses may be used each alone or in a combination thereof.

For example, the amine may include oleyl amine, dodecyl amine, lauryl amine, octyl amine, trioctyl amine, dioctyl amine, hexadecyl amine or the like. Theses may be used each alone or in a combination thereof.

Reaction of the first precursor and the organic acid may be processed by heating. For example, the reaction of the first precursor and the organic acid may be performed at a temperature of about 80° C. to about 150° C. Preferably, the reaction may be performed in a vacuum or in an inert condition including nitrogen gas, argon gas or the like.

Degassing may be further performed for promoting the reaction of the first precursor and the organic acid. Degassing may remove by-products of the reaction thereby moving reaction equilibrium of the first precursor and the organic acid. Thus, the reaction of the first precursor and the organic acid may be promoted. The degassing may be performed for about 1 hour to about 5 hours.

Thereafter, a second precursor reacts with a reaction product of the first precursor and the organic acid to form a quantum dot (S20). The second precursor may include at least one element selected from Groups 15 and 16.

For example, the second precursor may include tri-n-octylphosphine selenide, tri-n-butylphosphine selenide, diethyldiselenide, dimethylselenide, bis(trimethylsilyl)selenide, triphenylphosphine selenide (Se-TPP), tri-n-octylphosphine telluride, tri-n-butylphosphine telluride, bis(trimethylsilyl) telluride, triphenylphosphine telluride (Te-TPP), trioctylphosphine sulfide (S-TOP), tributylphosphine sulfide (S-TBP), triphenylphosphine sulfide (S-TPP), trioctylamine sulfide (S-TOA), bis(trimethylsilyl) sulfide, trimethylsilyl sulfide, ammonium sulfide, sodium sulfide or the like. Theses may be used each alone or in a combination thereof.

Reaction of the second precursor and the reaction product of the first precursor and the organic acid may be processed by heating. For example, the reaction may be performed at a temperature of about 80° C. to about 350° C., preferably at a temperature of about 80° C. to about 150° C.

Preferably, the reaction of the second precursor and the reaction product of the first precursor and the organic acid may be rapidly terminated by quenching. For example, the reaction may be terminated by hexane, ice water or the like.

Thereafter, a halogen compound is provided for stabilizing the quantum dot (S30). The reaction of the halogen compound and the quantum dot may be performed at a temperature higher than a room temperature, for example, at about 40° C. to about 80° C. Thus, the reaction solution cooled by quenching may be heated again to have an appropriate temperature.

The halogen compound is not limited to a particular compound, and may include any compound that may generate a halogen ion. Preferably, the halogen compound may include chlorine, bromine or iodine in view of bond energy. For example, the halogen compound may include a halogenated metal, an organic halide or the like. Particularly, the halogen compound may include tetrabutylammonium bromide, cetyltrimethylammonium bromide, ammonium chloride, ammonium bromide, ammonium iodide, potassium chloride, potassium bromide, potassium iodide, sodium chloride, sodium bromide, sodium iodide, indium chloride, indium bromide, indium iodide, or the like. Theses may be used each alone or in a combination thereof.

The halogen compound may be used with a solvent. For example, the solvent may include methanol, acetonitril, ethanol or the like.

Thereafter, unreacted monomers are removed (S40). A non-solvent such as alcohol is provided to the reaction solution to cause aggregation. Then, centrifugation is performed for precipitation. The precipitate is dispersed in a solvent to remove unreacted monomers. As a result, a stabilized quantum dot is obtained. The quantum dot may have a diameter of about 1 nm to about 100 nm, preferably about 1 nm to about 20 nm.

According to the exemplary embodiments of the present invention, a passivation layer is formed on a surface of a quantum dot by using a halogen salt. Thus, stability of the quantum dot in an air may be increased.

Hereinafter, examples of the present invention will be explained with reference to synthetic examples of a quantum dot.

Example 1

About 0.46 g of PbO was provided to a mixture solution including about 1.4 ml of oleic acid and about 10 ml of octadecyne. Then the mixture solution was heated at about 120° C. to prepare a precursor solution. After a temperature of the precursor solution was reduced to be about 90° C., a mixture including about 6 ml of trioctylphosphine selenide (6 M) and octadecyne. A reaction of the solution was quenched by hexane and ice water to form a quantum dot. After a temperature of the solution was increased to be about 60° C., about 0.19 M of ammonium chloride dispersed in methanol was provided to the solution and stirred. Thereafter, providing hexane and ethanol in a ratio of 1:2 to the solution and centrifuging were repeated three times to obtain PbSe quantum dot precipitate. A diameter of the quantum do, which was measured by transmission electron microscopy (TEM), was about 3 nm.

Example 2

A quantum dot was obtained through a substantially same method as Example 1 except using ammonium bromide instead of ammonium chloride.

Example 3

A quantum dot was obtained through a substantially same method as Example 1 except using ammonium iodide instead of ammonium chloride.

Example 4

A quantum dot was obtained through a substantially same method as Example 1 except using ammonium fluoride instead of ammonium chloride.

Example 5

A quantum dot was obtained through a substantially same method as Example 1 except using potassium chloride instead of ammonium chloride.

Example 6

A quantum dot was obtained through a substantially same method as Example 1 except using sodium chloride instead of ammonium chloride.

Example 7

A quantum dot was obtained through a substantially same method as Example 1 except using indium chloride instead of ammonium chloride.

Example 8

A quantum dot was obtained through a substantially same method as Example 1 except using tetrabutylammonium bromide instead of ammonium chloride.

Example 9

A quantum dot was obtained through a substantially same method as Example 1 except using cetyltrimethylammonium bromide instead of ammonium chloride.

Example 10

A quantum dot was obtained through a substantially same method as Example 1 except using tetrabutylammonium bromide and acetonitrile instead of ammonium chloride and methanol

Comparative Example 1

A quantum dot was obtained through a substantially same method as Example 1 except not providing ammonium chloride.

Figure 3A:
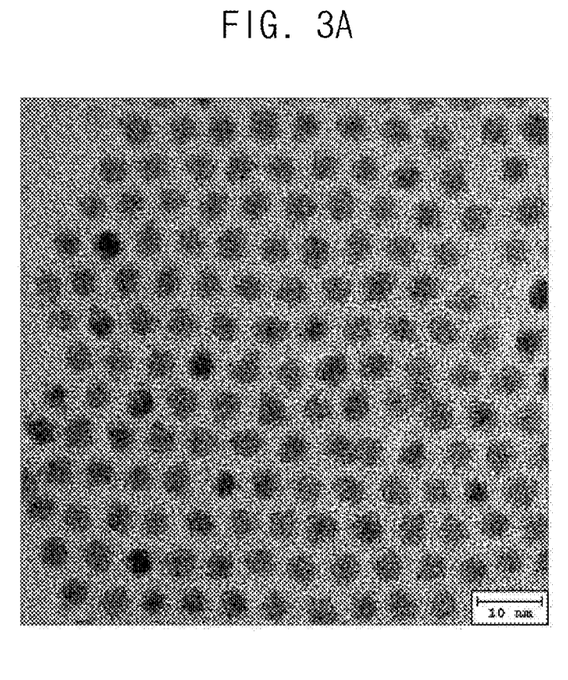
FIG. 3A is a TEM picture of Example 1.
Figure 3B:
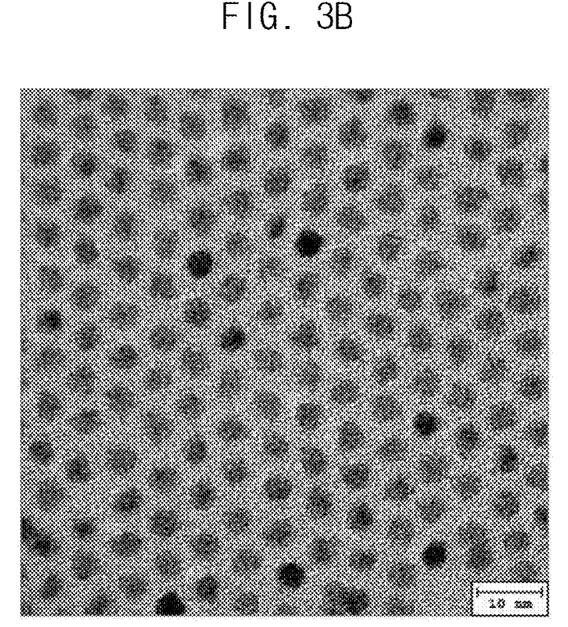
FIG. 3B is a TEM picture of Comparative Example 1.

FIG. 3A is a TEM picture of Example 1. FIG. 3B is a TEM picture of Comparative Example 1. Referring to FIGS. 3A and 3B, a size of the stabilized quantum of Example 1 is similar to the quantum dot of Comparative Example 1. Thus, it can be noted that a passivation layer formed by Example 1 for stabilizing is very thin so that the passivation layer hardly increases a size of the quantum dot.

Figure 4A:
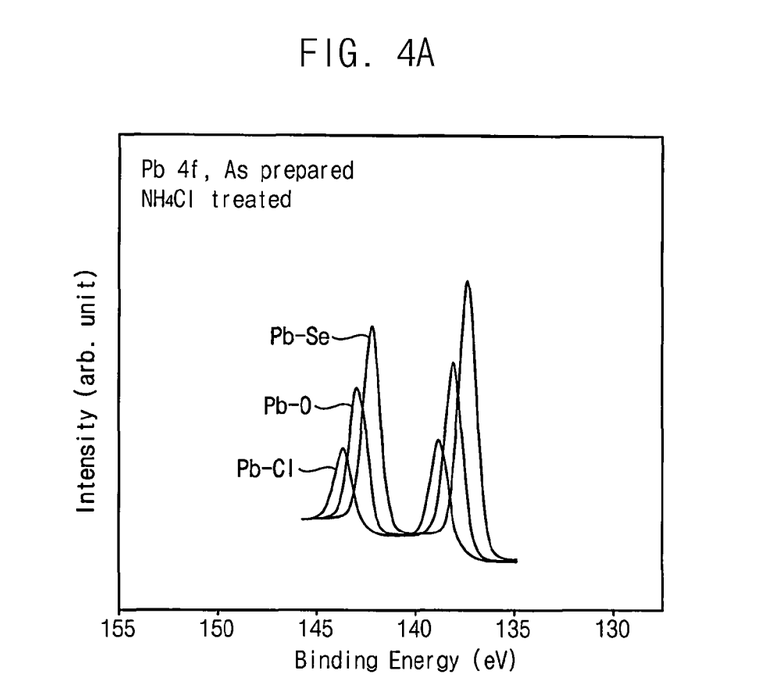
FIG. 4A is a graph showing XPS analysis of lead in the quantum dot of Example 1.
Figure 4B:
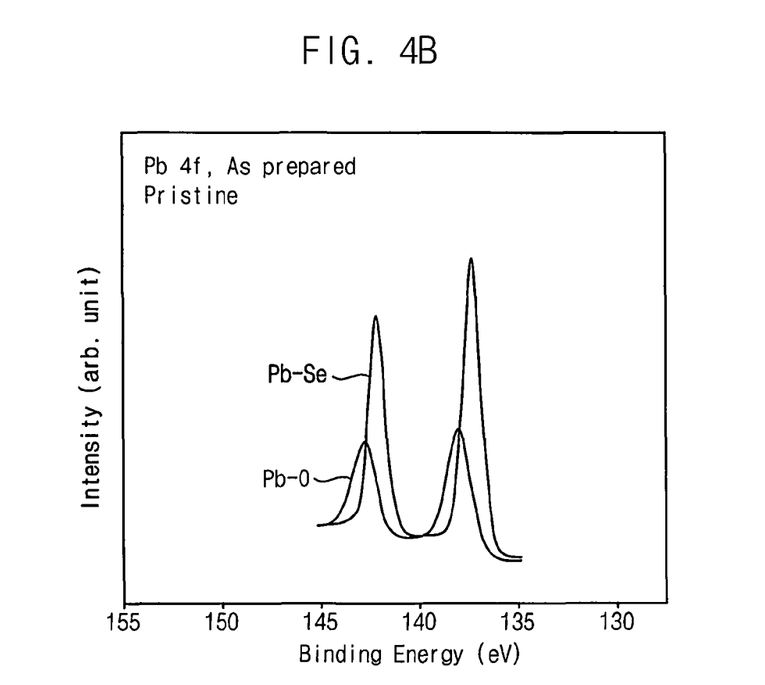
FIG. 4B is a graph showing XPS analysis of lead in the quantum dot of Comparative Example 1.

FIG. 4A is a graph showing XPS analysis of lead in the quantum dot of Example 1. FIG. 4B is a graph showing XPS analysis of lead in the quantum dot of Comparative Example 1. Referring to FIGS. 4A and 4B, it can be noted that the quantum dot includes an ionic bond of Pb—Cl, which is not shown in FIG. 4B for Comparative Example 1. Thus, it can be noted that a passivation layer of a halogen salt was formed in the quantum dot of Example 1. In FIGS. 4A and 4B, Pb—O peaks represents a bond of Pb and a ligand at a (111) surface.

Figure 5A:
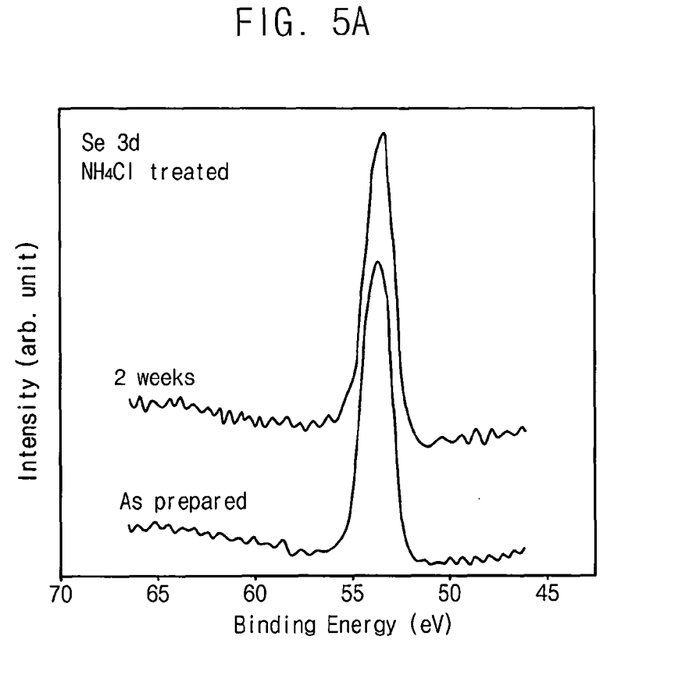
FIG. 5A is a graph showing XPS analysis of selenium in the quantum dot of Example 1.
Figure 5B:
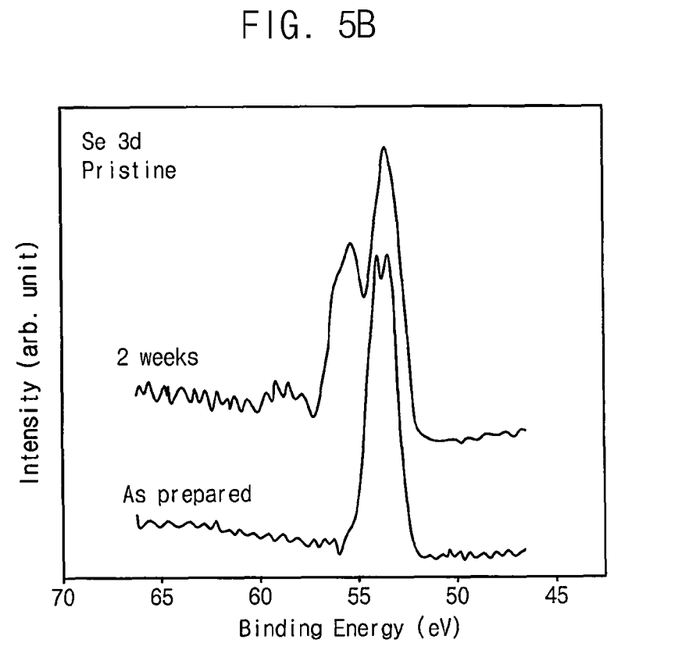
FIG. 5B is a graph showing XPS analysis of selenium in the quantum dot of Comparative Example 1.

FIG. 5A is a graph showing XPS analysis of selenium in the quantum dot of Example 1. FIG. 5B is a graph showing XPS analysis of selenium in the quantum dot of Comparative Example 1. The XPS analysis were firstly performed immediately after synthesis (As prepared), and second performed after lapse of two weeks in an air (2 weeks). Referring to FIGS. 5A and 5B, an amount of selenium in the quantum dot of Comparative Example 1 was reduced after lapse of two weeks in an air while an amount of selenium in the quantum dot of Example 1 was not substantially changed. Thus, it can be noted that the quantum dot of Example 1 may have a higher stability in an air than the quantum dot of Comparative Example 1.

Figure 6A:
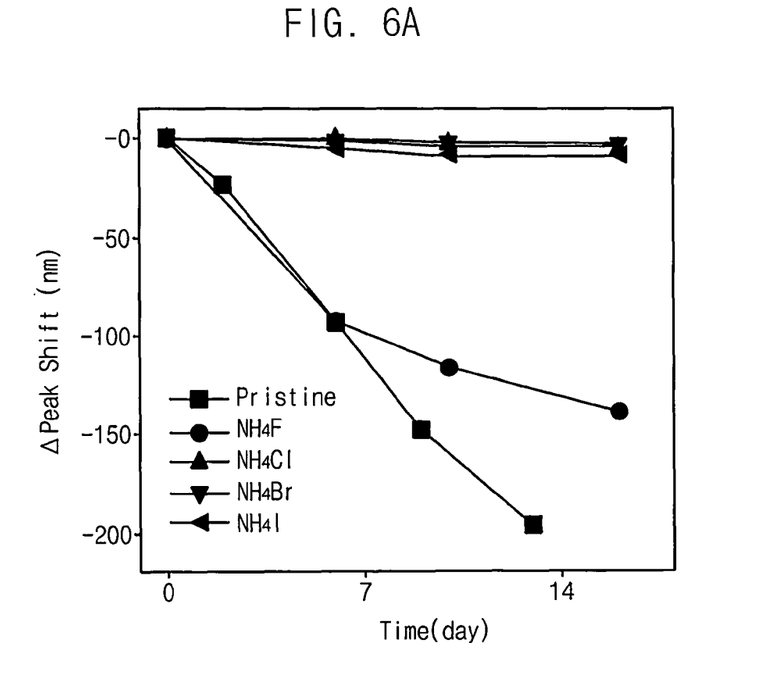
FIG. 6A is a graph showing absorption wavelength variation of the quantum dots of Examples 1 to 4 and Comparative Example 1 with respect to time.

FIG. 6A is a graph showing absorption wavelength variation of the quantum dots of Examples 1 to 4 and Comparative Example 1 with respect to time. Referring to FIG. 6A, an absorption wavelength of the quantum dot of Comparative Example 1 were changed according to time lapse while an absorption wavelength of the quantum dots of Examples 1 to 3 was not substantially changed. However, an absorption wavelength of the quantum dot of Examples 4 using fluoride was substantially changed.

Figure 6B:
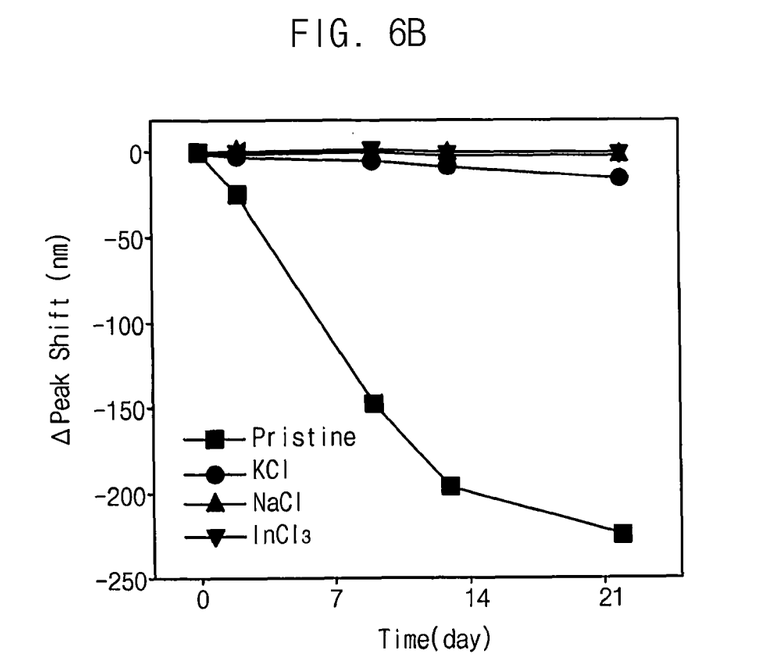
FIG. 6B is a graph showing absorption wavelength variation of the quantum dots of Examples 5 to 7 and Comparative Example 1 with respect to time.

FIG. 6B is a graph showing absorption wavelength variation of the quantum dots of Examples 5 to 7 and Comparative Example 1 with respect to time. Referring to FIG. 6B, it can be noted that various halogen salts can be used for stabilizing a quantum dot.

Figure 6C:
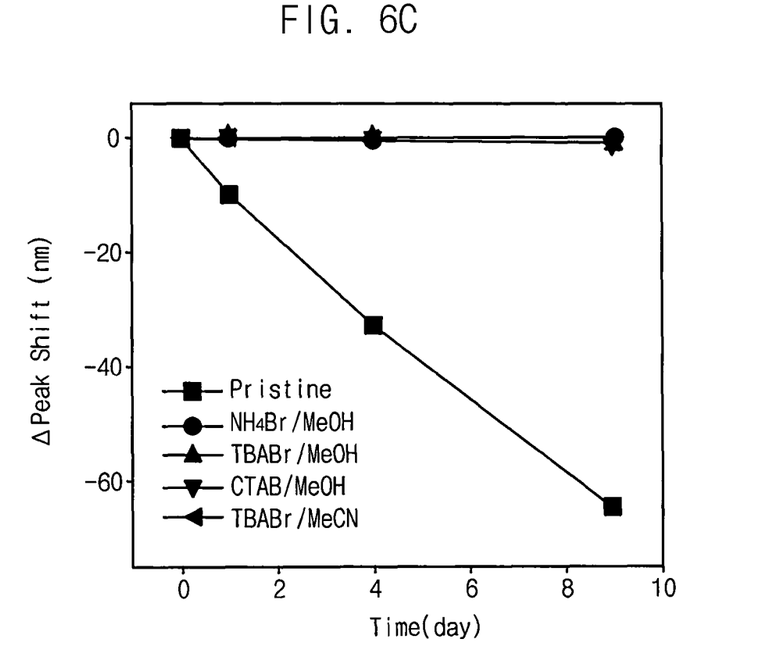
FIG. 6C is a graph showing absorption wavelength variation of the quantum dots of Examples 2, 8 and 10 and Comparative Example 1 with respect to time.

FIG. 6C is a graph showing absorption wavelength variation of the quantum dots of Examples 2, 8 and 10 and Comparative Example 1 with respect to time. Referring to FIG. 6C, it can be noted that various halogen salts and solvents can be used for stabilizing a quantum dot.

Exemplary embodiments of the present invention may be used for various electric elements, a transistor, a display device, a light source or the like.

The foregoing is illustrative and is not to be construed as limiting thereof. Although a few exemplary embodiments have been described, those skilled in the art will readily appreciate that many modifications are possible in the exemplary embodiments without materially departing from the novel teachings, aspects, and advantages of the invention. Accordingly, all such modifications are intended to be included within the scope of this disclosure.

What is claimed is:

1. A quantum dot stabilized by a halogen salt, the quantum dot comprising a compound of Group 13 and Group 15, a compound of Group 12 and Group 16 or a compound of Group 14 and Group 16, wherein the quantum dot has a crystalline structure and at least a portion of a surface of the quantum dot is combined with a halogen salt,
  wherein the quantum dot has a first surface combined with the halogen salt and a second surface combined with an organic ligand.

2. The quantum dot of claim 1, wherein a diameter of the quantum dot is 1 nm to 20 nm.

3. The quantum dot of claim 1, wherein the first surface combined with the halogen salt is a (100) surface, and the second surface combined with the organic ligand is a (111) surface.

4. The quantum dot of claim 1, wherein the compound of Group 14 and Group 16 comprises at least one selected from the group consisting of tin oxide (SnO), tin sulfide (SnS), tin selenide (SnSe), tin telluride (SnTe), lead sulfide (PbS), lead selenide (PbSe), lead telluride (PbTe), germanium oxide (GeO), germanium sulfide (GeS), germanium selenide (GeSe), germanium telluride (GeTe), tin selenium sulfide (SnSeS), tin selenium telluride (SnSeTe), tin sulfide telluride (SnSTe), lead selenium sulfide (PbSeS), lead selenium telluride (PbSeTe), lead sulfide telluride (PbSTe), tin lead sulfide (SnPbS), tin lead selenide (SnPbSe), tin lead telluride (SnPbTe), tin oxide sulfide (SnOS), tin oxide selenide (SnOSe), tin oxide telluride (SnOTe), germanium oxide sulfide (GeOS), germanium oxide selenide (GeOSe), germanium oxide telluride (GeOTe), tin lead sulfide selenide (SnPbSSe), tin lead selenium telluride (SnPbSeTe) and tin lead sulfide telluride (SnPbSTe).

5. The quantum dot of claim 1, wherein the compound of Group 13 and Group 15 comprises at least one selected from the group consisting of gallium phosphide (GaP), gallium arsenide (GaAs), gallium antimonide (GaSb), gallium nitride (GaN), aluminum phosphide (AlP), aluminum arsenide (AlAs), aluminum antimonide (AlSb), aluminum nitride (AlN), indium phosphide (InP), indium arsenide (InAs), indium antimonide (InSb), indium nitride (InN), gallium phosphide arsenide (GaPAs), gallium phosphide antimonide (GaPSb), gallium phosphide nitride (GaPN), gallium arsenide nitride (GaAsN), gallium antimonide nitride (GaSbN), aluminum phosphide arsenide (AlPAs), aluminum phosphide antimonide (AlPSb), aluminum phosphide nitride (AlPN), aluminum arsenide nitride (AlAsN), aluminum antimonide nitride (AlSbN), indium phosphide arsenide (InPAs), indium phosphide antimonide (InPSb), indium phosphide nitride (InPN), indium arsenide nitride (InAsN), indium antimonide nitride (InSbN), aluminum gallium phosphide (AlGaP), aluminum gallium arsenide (AlGaAs), aluminum gallium antimonide (AlGaSb), aluminum gallium nitride (AlGaN), aluminum arsenide nitride (AlAsN), aluminum antimonide nitride (AlSbN), indium gallium phosphide (InGaP), indium gallium arsenide (InGaAs), indium gallium antimonide (InGaSb), indium gallium nitride (InGaN), indium arsenide nitride (InAsN), indium antimonide nitride (InSbN), aluminum indium phosphide (AlInP), aluminum indium arsenide (AlInAs), aluminum indium antimonide (AlInSb), aluminum indium nitride (AlInN), aluminum arsenide nitride (AlAsN), aluminum antimonide nitride (AlSbN), aluminum phosphide nitride (AlPN), gallium aluminum phosphide arsenide (GaAlPAs), gallium aluminum phosphide antimonide (GaAlPSb), gallium indium phosphide arsenide (GaInPAs), gallium indium aluminum arsenide (GaInAlAs), gallium aluminum phosphide nitride (GaAlPN), gallium aluminum arsenide nitride (GaAlAsN), gallium aluminum antimonide nitride (GaAlSbN), gallium indium phosphide nitride (GaInPN), gallium indium arsenide nitride (GaInAsN), gallium indium aluminum nitride (GaInAlN), gallium antimonide phosphide nitride (GaSbPN), gallium arsenide phosphide nitride (GaAsPN), gallium arsenide antimonide nitride (GaAsSbN), gallium indium phosphide antimonide (GaInPSb), gallium indium phosphide nitride (GaInPN), gallium indium antimonide nitride (GaInSbN), gallium phosphide antimonide nitride (GaPSbN), indium aluminum phosphide arsenide (InAlPAs), indium aluminum phosphide nitride (InAlPN), indium phosphide arsenide nitride (InPAsN), indium aluminum antimonide nitride (InAlSbN), indium phosphide antimonide nitride (InPSbN), indium arsenide antimonide nitride (InAsSbN) and indium aluminum phosphide antimonide (InAlPSb).

6. The quantum dot of claim 1, wherein the compound of Group 12 and Group 16 comprises at least one selected from the group consisting of cadmium sulfide (CdS), cadmium selenide (CdSe), cadmium telluride (CdTe), zinc sulfide (ZnS), zinc selenide (ZnSe), zinc telluride (ZnTe), mercury sulfide (HgS), mercury selenide (HgSe), mercury telluride (HgTe), zinc oxide (ZnO), cadmium oxide (CdO), mercury oxide (HgO), cadmium selenium sulfide (CdSeS), cadmium selenium telluride (CdSeTe), cadmium sulfide telluride (CdالسTe), cadmium zinc sulfide (CdZnS), cadmium zinc selenide (CdZnSe), cadmium sulfide selenide (CdSSe), cadmium zinc telluride (CdZnTe), cadmium mercury sulfide (CdHgS), cadmium mercury selenide (CdHgSe), cadmium mercury telluride (CdHgTe), zinc selenium sulfide (ZnSeS), zinc selenium telluride (ZnSeTe), zinc sulfide telluride (ZnSTe), mercury selenium sulfide (HgSeS), mercury selenium telluride (HgSeTe), mercury sulfide telluride (HgSTe), mercury zinc sulfide (HgZnS), mercury zinc selenide (HgZnSe), cadmium zinc oxide (CdZnO), cadmium mercury oxide (CdHgO), zinc mercury oxide (ZnHgO), zinc selenium oxide (ZnSeO), zinc tellurium oxide (ZnTeO), zinc sulfide oxide (ZnSO), cadmium selenium oxide (CdSeO), cadmium tellurium oxide (CdTeO), cadmium sulfide oxide (CdSO), mercury selenium oxide (HgSeO), mercury tellurium oxide (HgTeO), mercury sulfide oxide (HgSO), cadmium zinc selenium sulfide (CdZnSeS), cadmium zinc selenium telluride (CdZnSeTe), cadmium zinc sulfide telluride (CdZnSTe), cadmium mercury selenium sulfide (CdHgSeS), cadmium mercury selenium telluride (CdHgSeTe), cadmium mercury sulfide telluride (CdHgSTe), mercury zinc selenium sulfide (HgZnSeS), mercury zinc selenium telluride (HgZnSeTe), mercury zinc sulfide telluride (HgZnSTe), cadmium zinc selenium oxide (CdZnSeO), cadmium zinc tellurium oxide (CdZnTeO), cadmium zinc sulfide oxide (CdZnSO), cadmium mercury selenium oxide (CdHgSeO), cadmium mercury tellurium oxide (CdHgTeO), cadmium mercury sulfide oxide (CdHgSO), zinc mercury selenium oxide (ZnHgSeO), zinc mercury tellurium oxide (ZnHgTeO) and zinc mercury sulfide oxide (ZnHgSO).

* * * * *